US008556074B2

(12) United States Patent
Turner et al.

(10) Patent No.: US 8,556,074 B2
(45) Date of Patent: Oct. 15, 2013

(54) ENCAPSULATED DATA CARRIER TAG FOR TRACK AND TRACE PURPOSES

(75) Inventors: Robin Turner, Memphis, TN (US); Thor Hanna, Memphis, TN (US); Marc Deason, Germantown, TN (US)

(73) Assignee: Warsaw Orthopedic, Inc, Warsaw, IN (US)

( * ) Notice: Subject to any disclaimer, the term of this patent is extended or adjusted under 35 U.S.C. 154(b) by 0 days.

(21) Appl. No.: 13/281,109

(22) Filed: Oct. 25, 2011

(65) Prior Publication Data

US 2013/0103150 A1 Apr. 25, 2013

(51) Int. Cl.
*B65D 85/24* (2006.01)
*A61F 2/02* (2006.01)

(52) U.S. Cl.
USPC ......... 206/363; 206/339; 206/438; 206/459.5

(58) Field of Classification Search
USPC ......... 206/363, 339, 807, 63.5, 570, 438, 1.5, 206/459.5; 235/385, 375, 285; 340/572.1, 340/572.8; 606/71
See application file for complete search history.

(56) References Cited

U.S. PATENT DOCUMENTS

| | | | |
|---|---|---|---|
| 4,154,342 A | 5/1979 | Wallace | |
| 4,501,363 A | 2/1985 | Isbey, Jr. | |
| 4,553,669 A | 11/1985 | Butterworth et al. | |
| 4,856,648 A | 8/1989 | Krueger | |
| 4,883,193 A * | 11/1989 | Christensson | 220/266 |
| 5,199,567 A | 4/1993 | Discko, Jr. | |
| 5,636,736 A | 6/1997 | Jacobs | |
| 5,759,028 A | 6/1998 | Bozman | |
| 5,762,192 A | 6/1998 | Jacobs | |
| 5,788,105 A * | 8/1998 | Foos | 220/266 |
| 5,887,707 A | 3/1999 | Anascavage | |
| 5,934,460 A | 8/1999 | Schmid | |
| 5,934,486 A * | 8/1999 | Jarvis et al. | 211/41.8 |
| 5,967,305 A | 10/1999 | Blonder | |
| 5,996,779 A * | 12/1999 | Klardie et al. | 206/63.5 |

(Continued)

FOREIGN PATENT DOCUMENTS

DE 202007004638 6/2007
EP 1842505 10/2007

(Continued)

OTHER PUBLICATIONS

International Search Report in realted Application No. PCT/US2009041760, mailed Aug. 11, 2009.

(Continued)

*Primary Examiner* — Steven A. Reynolds

(57) ABSTRACT

A tag for tracking inventory levels and uses of an implant. The tag has a first component having a proximal portion and a distal portion and a second component having a proximal portion and distal portion. Additionally, the tag has an implant receiving cavity formed by the distal portion of the first component and the distal portion of the second component, in which the implant receiving cavity includes an encapsulating extension to substantially encapsulate an implant. Furthermore, the tag has a planar surface formed by the proximal portion of the first component and the proximal portion of the second component. The planar surface extending from the implant receiving cavity is substantially transverse to a longitudinal axis of the implant received within the implant receiving cavity. In addition, the tag has a tamper evident locking mechanism configured for locking the first component to the second component.

19 Claims, 8 Drawing Sheets

(56) References Cited

U.S. PATENT DOCUMENTS

| | | | |
|---|---|---|---|
| 6,328,746 B1 | 12/2001 | Gambale | |
| 6,346,109 B1 * | 2/2002 | Fucci et al. | 606/104 |
| 6,373,786 B1 | 4/2002 | Kagan | |
| 6,375,956 B1 | 4/2002 | Hermelin | |
| 6,415,916 B1 | 7/2002 | Rini | |
| 6,886,688 B2 * | 5/2005 | Sykes et al. | 206/308.2 |
| 6,929,646 B2 * | 8/2005 | Gambale | 606/71 |
| 7,048,120 B2 | 5/2006 | Pond | |
| 7,118,029 B2 | 10/2006 | Nycz et al. | |
| 7,213,767 B2 | 5/2007 | Tethrake et al. | |
| 7,256,699 B2 | 8/2007 | Tethrake et al. | |
| 7,268,684 B2 | 9/2007 | Tethrake et al. | |
| 7,338,282 B2 | 3/2008 | Corcoran | |
| 7,362,228 B2 | 4/2008 | Nycz et al. | |
| 7,490,723 B2 * | 2/2009 | Levisman | 206/368 |
| 8,061,517 B2 * | 11/2011 | Loeffler et al. | 206/339 |
| 8,083,054 B2 * | 12/2011 | Nihei et al. | 206/63.5 |
| 8,181,773 B2 * | 5/2012 | Guenter et al. | 206/63.5 |
| 2002/0004660 A1 | 1/2002 | Henniges | |
| 2003/0033016 A1 * | 2/2003 | Dees, Jr. | 623/10 |
| 2003/0221977 A1 * | 12/2003 | Kumar et al. | 206/63.5 |
| 2004/0243207 A1 | 12/2004 | Olson | |
| 2005/0033430 A1 | 2/2005 | Powers et al. | |
| 2006/0124485 A1 * | 6/2006 | Kennedy | 206/340 |
| 2006/0144749 A1 | 7/2006 | Arnold | |
| 2006/0145871 A1 | 7/2006 | Donati | |
| 2006/0244652 A1 | 11/2006 | Tethrake et al. | |
| 2006/0260958 A1 | 11/2006 | Brunner | |
| 2007/0001839 A1 | 1/2007 | Cambre et al. | |
| 2007/0095689 A1 | 5/2007 | Pratt et al. | |
| 2007/0125392 A1 | 6/2007 | Olson et al. | |
| 2007/0144926 A1 | 6/2007 | Bettenhausen et al. | |
| 2007/0159337 A1 | 7/2007 | Tethrake et al. | |
| 2007/0188306 A1 | 8/2007 | Tethrake et al. | |
| 2007/0205126 A1 | 9/2007 | Elsener | |
| 2007/0227917 A1 * | 10/2007 | Foust | 206/63.5 |
| 2007/0239289 A1 | 10/2007 | Cambre et al. | |
| 2007/0284428 A1 | 12/2007 | Cambre et al. | |
| 2007/0295620 A1 * | 12/2007 | Collet et al. | 206/63.5 |
| 2008/0048855 A1 | 2/2008 | Berger | |
| 2008/0230421 A1 | 9/2008 | Pleil et al. | |
| 2008/0230422 A1 | 9/2008 | Pleil et al. | |
| 2008/0230423 A1 | 9/2008 | Loeffler et al. | |
| 2009/0065376 A1 * | 3/2009 | Donahoe et al. | 206/63.5 |
| 2009/0118831 A1 | 5/2009 | Trieu | |
| 2009/0266728 A1 * | 10/2009 | Turner et al. | 206/363 |
| 2009/0266890 A1 | 10/2009 | Bagozzi | |
| 2011/0114514 A1 * | 5/2011 | Bagozzi et al. | 206/216 |

FOREIGN PATENT DOCUMENTS

| | | |
|---|---|---|
| JP | 2008052013 | 3/2008 |
| KR | 1020060102826 | 9/2006 |
| WO | 2006124188 | 11/2006 |

OTHER PUBLICATIONS

INternational Searching AUthority, IRS and Written Opinion, Jul. 31, 2009.

Orthopedics This Week, vol. 4, Issue 4, p. 4, Feb. 5, 2008, "Radio Frequency Identification and Orthopedics."

* cited by examiner

ENCAPSULATED DATA CARRIER TAG FOR TRACK AND TRACE PURPOSES

RELATED APPLICATIONS

This application is related to U.S. patent application Ser. No. 12/109,517, filed Apr. 25, 2008, to U.S. patent application Ser. No. 12/109,534, filed Apr. 25, 2008, to U.S. patent application Ser. No. 12/109,539, filed Apr. 25, 2008, and to U.S. patent application Ser. No. 12/512,274, filed Jul. 30, 2009, the disclosures of each of which are entirely incorporated herein by reference.

BACKGROUND

There is a need to track non-sterile medical devices from their base materials and manufacture to their use, and throughout the intervening time. A non-sterile medical device is a medical device that is shipped from a manufacturer in a condition that is not adequately sterilized for implantation. By contrast, a sterile medical device is shipped from the manufacture in a condition adequately sterilized for implantation. Healthcare providers may prefer to receive non-sterile medical devices for various reasons. In that regard, because non-sterile devices can be sterilized onsite before a medical procedure, non-sterile medical devices having a longer shelf life than a corresponding sterile medical device. Furthermore, non-sterile medical devices are less expensive to package. Additionally, non-sterile medical devices typically can be more densely packaged into a common carrier than sterile devices.

U.S. Patent Application Publication No. 2008/0230423 discloses a holding device for an implant in which the implant can be releasably attached from the holding device and the storage unit. The locking mechanism can be activated and released to release the implant, and optionally may contain an indicating element that provides an indication that the implant has been released from the holding device.

Difficulty arises in tracking non-sterile medical devices. For example, non-sterile medical devices are difficult to track because medical devices generally do not have adequate surface area for applying marks. Thus, in many instances, non-sterile medical devices are not tracked beyond their manufacturing facility, and may only be counted when reconciled for payment as one of many products that were not returned to a manufacturer for replenishment.

Accordingly, devices, systems and methods for tracking and tracing non-sterile medical devices are needed.

SUMMARY

Disclosed herein is a tag for tracking inventory levels and uses of an implant. The tag has a first component having a proximal portion and a distal portion and a second component having a proximal portion and distal portion. Additionally, the tag has an implant receiving cavity formed by the distal portion of the first component and the distal portion of the second component, whereby the implant receiving cavity includes an encapsulating extension to substantially encase or encapsulate the implant. Furthermore, the tag has a planar surface formed by the proximal portion of the first component and the proximal portion of the second component. The planar surface extending from the implant receiving cavity such that the planar surface is substantially transverse to a longitudinal axis of the implant received within the implant receiving cavity. Also, the planar surface includes indicia and one or more extensions to secure the implant within the tag and prevent it from falling out during transport and handling. In addition, the tag has a tamper evident locking mechanism configured for locking the first component to the second component. Additionally, at least a portion of the first and second components is radiopaque.

Another embodiment described herein includes a system that includes the tag described above, and an implant encapsulated within the tag. These and other aspects, forms, objects, features, and benefits of the present invention will become apparent from the following detailed drawings and description.

BRIEF DESCRIPTION OF THE DRAWINGS

In the accompanying drawings, which are incorporated in and constitute a part of the specification, embodiments of the invention are illustrated, which, together with a general description of the invention given above, and the detailed description given below, serve to exemplify the embodiments of this invention.

DETAILED DESCRIPTION

Figure 1:
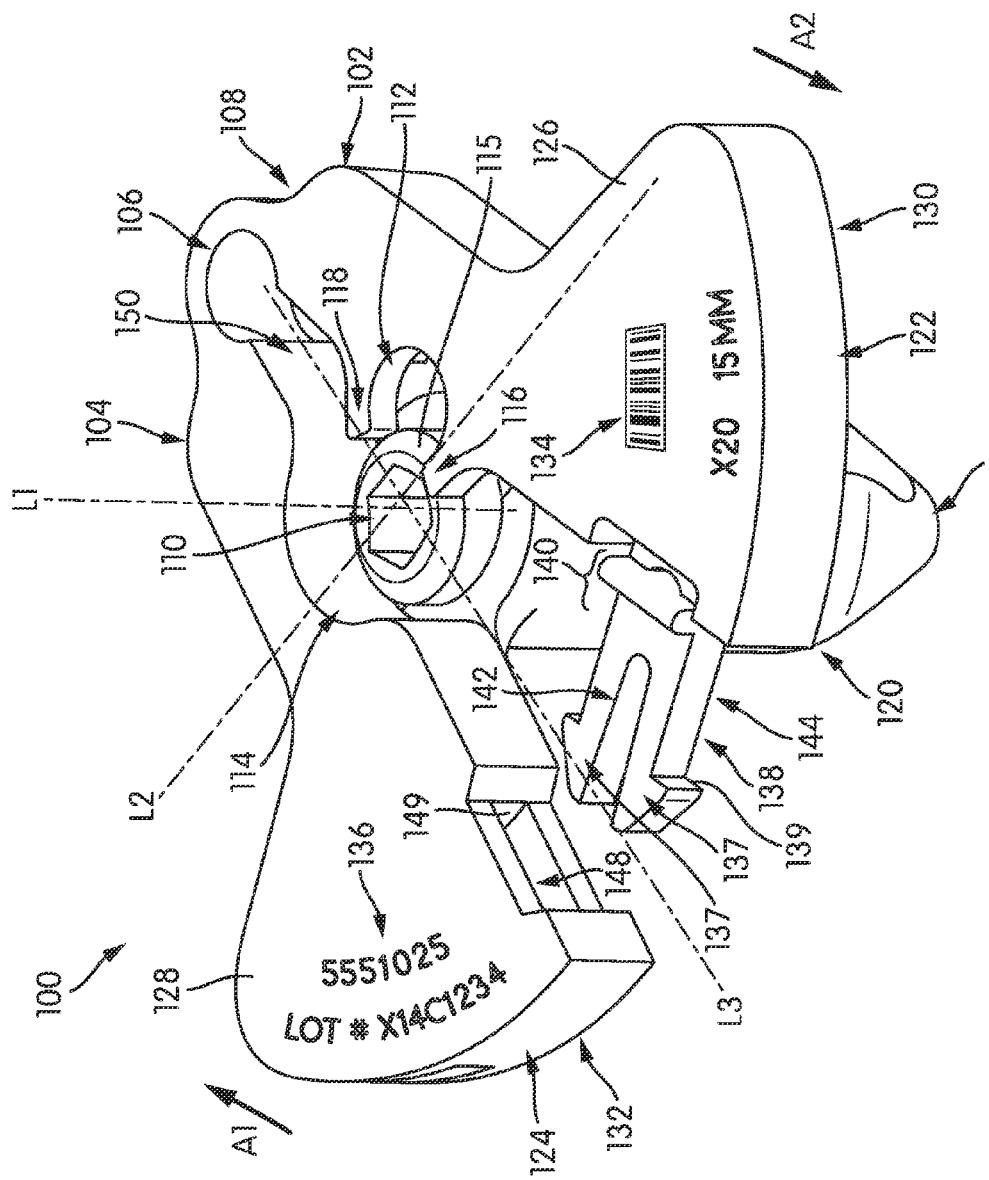
FIG. 1 is a perspective view of a tag for attachment to a medical device according to one embodiment of the present disclosure.

The present disclosure relates generally to the field of orthopedic surgery, and more particularly to devices, systems and methods for tracking and tracing medical devices through the use of removable tags. For the purposes of promoting an understanding of the principles of the invention, reference will now be made to embodiments or examples illustrated in the drawings, and specific language will be used to describe these examples. It will nevertheless be understood that no limitation of the scope of the invention is thereby intended. Any alteration and further modifications in the described embodiments, and any further applications of the principles of the invention as described herein, are contemplated as would normally occur to one skilled in the art to which the disclosure relates.

Referring first to FIG. 1, a perspective view of a tag 100 for attachment to a medical device is shown. Tag 100 is shown in an open or unlocked position ready to capture a medical device. Tag 100 has a first component 102 and second component 104. A hinge or web 106 flexibly connects the first component 102 and second component 104 to each other at a distal portion 108 of tag 100. Web 106 provides sufficient flexibility to allow the first and second components to move relative to each other along axes L1 (y-axis), L2 (x-axis), L3 (z-axis), and any intervening axis. In that regard, web 106 allows the first component 102 and second component 104 to remain attached to one another while the first and second components are positioned to capture a medical device therebetween.

Figure 2:
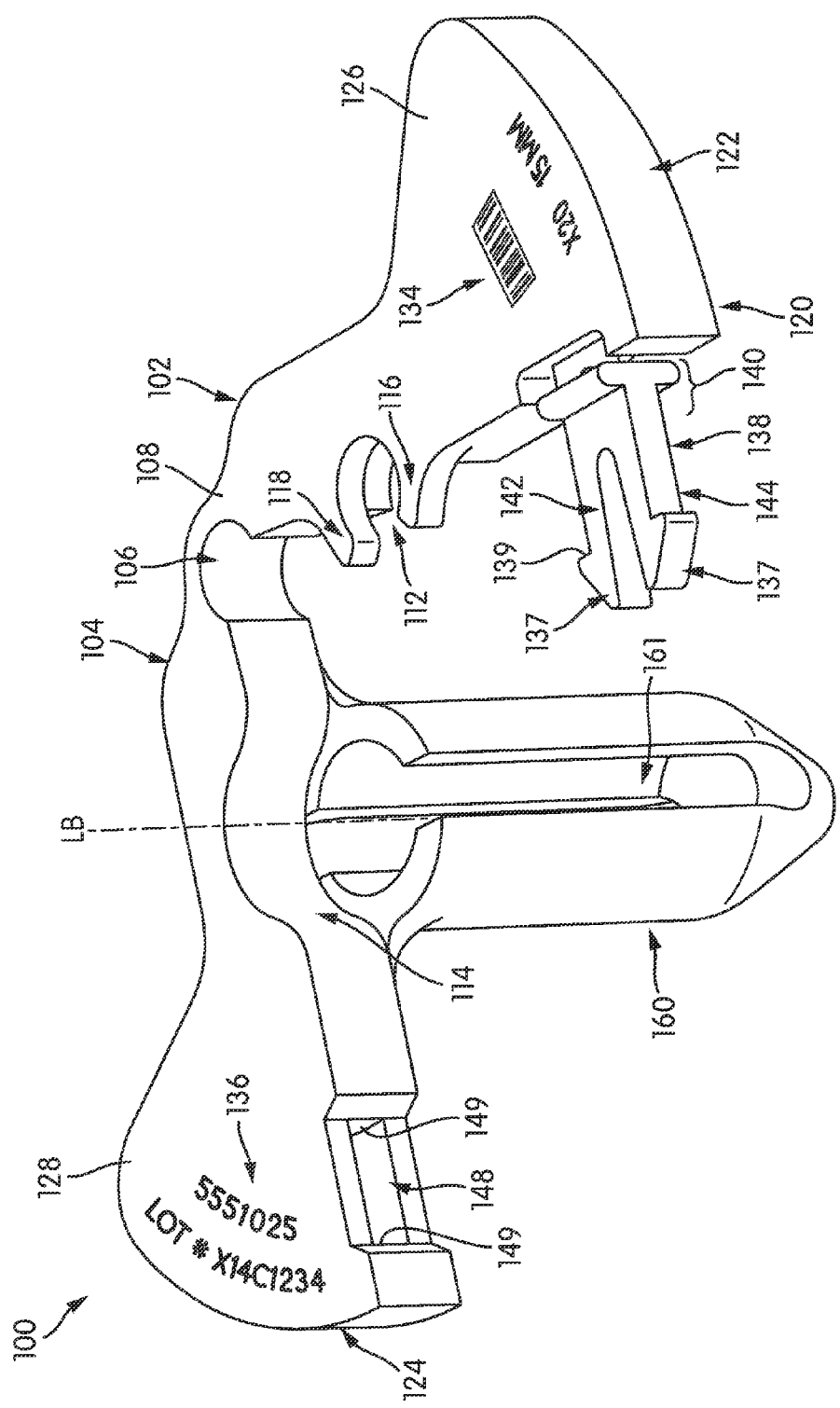
FIG. 2 is a perspective view of the tag of FIG. 1 where the tag is in an unlocked position.

Additionally, the distal portion of tag 100 defines an implant or medical device receiving cavity 110. In particular, portions 112 and 114 (FIG. 2) of the first and second components 102, 104 define the implant receiving cavity 110. As shown in FIG. 1, cavity 110 has a circular shape to receive a medical device with the corresponding shape. Tag 100 further includes an encapsulating extension 160 attached to first or second components 102, 104 (shown attached to second component 104 in FIGS. 1 and 2, but these illustrations are not limiting) capable of substantially encapsulating the medical device or implant. It is preferred that encapsulating extension 160 include one or more extending slots 161 to facilitate sterilization of the device. While encapsulating extension 160 is shown with one or more extending slots 161, an alternative embodiment may be provided in which encapsulating extension 160 may fully encapsulate the device, and contain one or more apertures (not shown) to facilitate sterilization of the device. While the cavity 110 and encapsulating extension 160 shown in FIGS. 1 and 2 illustrate the encapsulation of a screw, it is contemplated that cavity 110 and encapsulating extension 160 can be any shape in order to accommodate the medical device. For example, implant receiving cavity 110 and encapsulating extension 160 can be semi-circular, semi-rectangular, square, rectangular, trapezoidal, oblong, cylindrical, triangular, and any other shape necessary to receive the medical device within the cavity 110.

Furthermore, implant receiving cavity 110 is designed to allow at least a portion of a medical device to extend through cavity 110. Additionally, it is contemplated that a portion of the medical device may extend from above and/or below cavity 110 while tag 100 is attached to the device.

Figure 4:
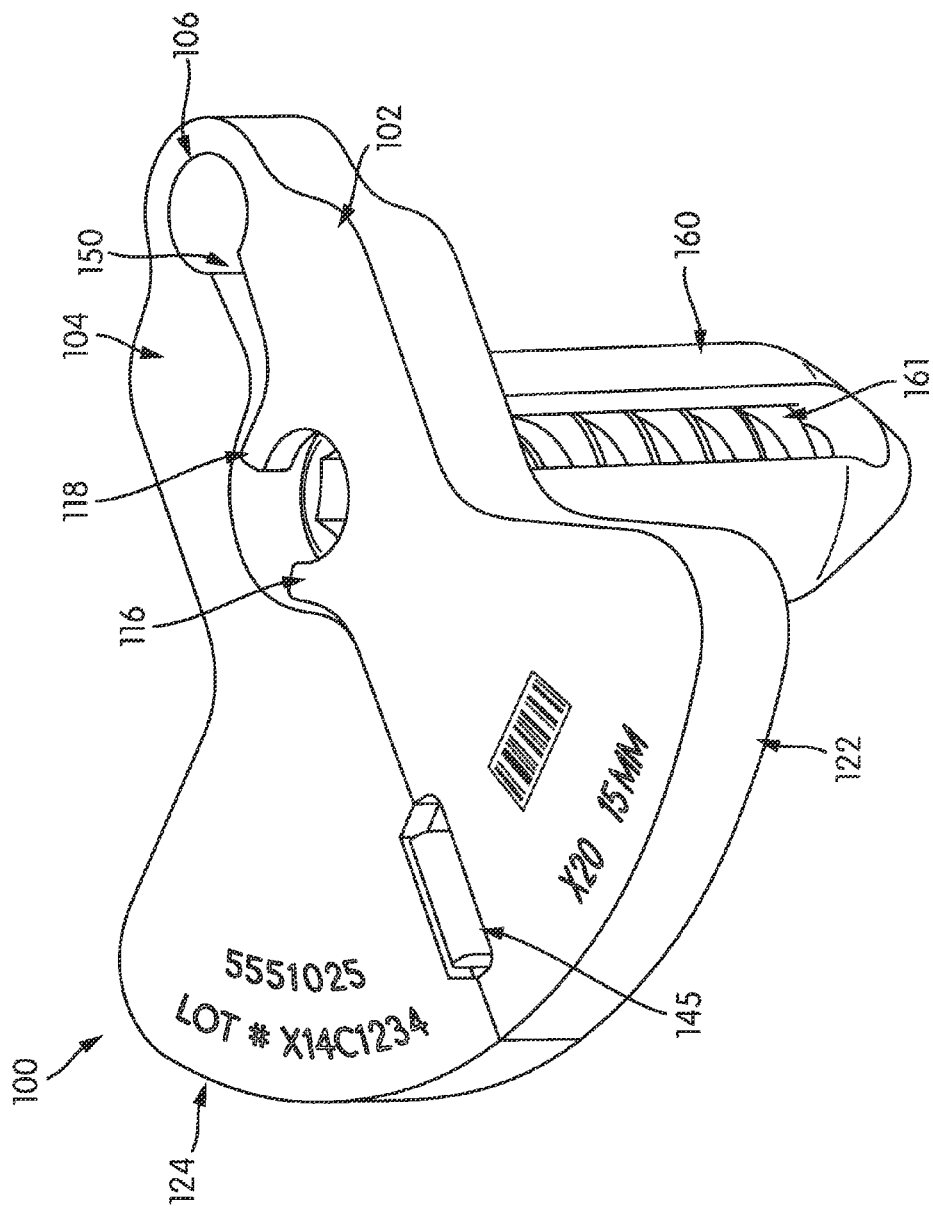
FIG. 4 is a perspective view of the tag of FIGS. 1 and 2 in a locked position.

First or second components 102, 104 further preferably include extensions 116 and 118 (shown attached to first component 102 in FIGS. 1 and 2, but these illustrations are not limiting). In this regard, extensions 116 and 118 are designed to further secure a medical device within cavity 110 when tag 100 is in a closed or locked position as shown in FIG. 4. FIG. 4 illustrates tag 100 securely encapsulating the medical device and preventing its removal from that tag 100 without permanently deforming the tag 100. Use of extensions 116 and 118, together with encapsulating extension 160, provides tag 100 and encapsulated device in rotational alignment with one another.

Tag 100 further comprises a pair of lobes 122 and 124 that extend from implant receiving cavity 110 toward a proximal portion 120 of tag 100. As shown in FIG. 1, lobes 122 and 124 extend along a plane substantially transverse from axis L1 or, as shown in FIG. 2, substantially transverse from a longitudinal axis LB of encapsulating extension 160. However, lobes 122 and 124 can extend at any angle with respect to axis L1 or L3.

Lobes 122 and 124 have upper planar surfaces 126 and 128 and opposing lower surfaces 130 and 132, respectively. Upper planar surfaces 126 and 128 provide a relatively large planar surface with respect to any portion of a medical device captured by tag 100. In this manner, upper planar surface 126 and 128 provide an ideal surface for applying indicia or markings relevant to a medical device captured by tag 100.

As shown in FIG. 1, upper planar surface 126 and 128 contain indicia 134 and 136. Indicia 134 and 136 represent markings or tracking devices capable of retaining identifying information, for example, relevant to the medical device captured by tag 100. Additionally, indicia 134 and 136 may represent identifying information related to the patient receiving the device, medical procedure used with the device, manufacturing information such as materials, processes, customer/supplier, and lot information of similarly manufactured devices. The identifying information is not intended to be limiting in scope by this disclosure, but instead is presented for exemplarily purposes only. Furthermore, any required manufacturing standards requiring the marking of products with certain identifying information is considered to be within the scope of identifying information capable of be represented by indicia 134 and 136. Therefore, there is no need for the medical device captured by tag 100 to have identifying information because tag 100 provides any necessary identifying information. Furthermore, because it is not possible to remove the medical device from the tag 100 without breaking at least a portion of the tag 100 (explained in more detail below with reference to FIG. 3), the medical device captured by tag 100 can be more accurately and reliably tracked, when compared to holding devices that can release the implant without destroying the tag.

In the embodiment illustrated in FIGS. 1 and 2, indicia 134 and 136 represent a two dimensional bar code and alphanumeric lettering, respectively used to identify a medical device captured by tag 100. However, indicia 134 and 136, or any tracking device herein, may be any device that is capable of retaining identifying information. For example, the indicia can be a one or two dimensional barcode capable of being scanned by an optical scanner. Such an optical scanner may include a barcode scanner made by Baracoda such as the Evolution scanner (part number: B40160202).

Preferably, the tracking device or indicia may be in the form of a radio frequency identification (REID) device built into one or both the lobes 122, 124 of tag 100. Such an RFID device can transmit a radio frequency signal to an RFID transceiver that can obtain the identifying information of the medical device stored in the RFID device. Additionally, the indicia can include, for example, human readable information and/or data that may include visual alphanumeric characters and tactile features such as different surface textures and/or raised or lowered portions. Furthermore, the lobes 122 and 124 can include a sealable groove, slot, or compartment (not shown) that has a transparent cover such that any human and/or computer readable information can be placed into the sealable groove, slot, or compartment, but can still be read through upper planar surfaces 126 and 128. In addition, the indicia may include a printed adhesive label in either human and/or computer readable form that is resistant to degradation during sterilization procedures.

Furthermore, although indicia 134 and 136 are shown as two separate types of tracking devices, the identifying information contained within these indicia may contain the same amount of identifying information. However, it is also possible that one indicia may provide more identifying information than the other indicia. Additionally, there may be only one indicia on either lobe 122 or lobe 124, but not the other lobe. Furthermore, the same type of indicia may be represented on both lobes 122 and 124. Even more, lobes 122 and 124 may have only one indicia that spans consecutively across both upper planar surfaces 126 and 128. It is preferred that the indicia be capable of withstanding the rigors of medical device sterilization. Accordingly, when the tag 100 contains a medical device that is part of a larger surgical procedure tray or kit, if the particular medical device encapsulated by tag 100 were not used in a given procedure, the medical device, together with the tag 100 could be re-sterilized (multiple times if necessary), and re-used. And because the tag 100 contains a tamper evident locking mechanism (described below), the medical device can be reliably traced and tracked throughout its life cycle.

Lobes 122 and 124 further contain a tamper evident locking mechanism that locks the first component 102 to the second component 104. Preferably, lobe 122 has a fork-like projection 138 located on the most proximal portion of tag 100. Fork-like projection 138 has a frangible connection to lobe 122. The frangible connection is created by a connection mechanism 140 extending along the width W of fork-like projection 138 at its connection with lobe 122.

Figure 3:
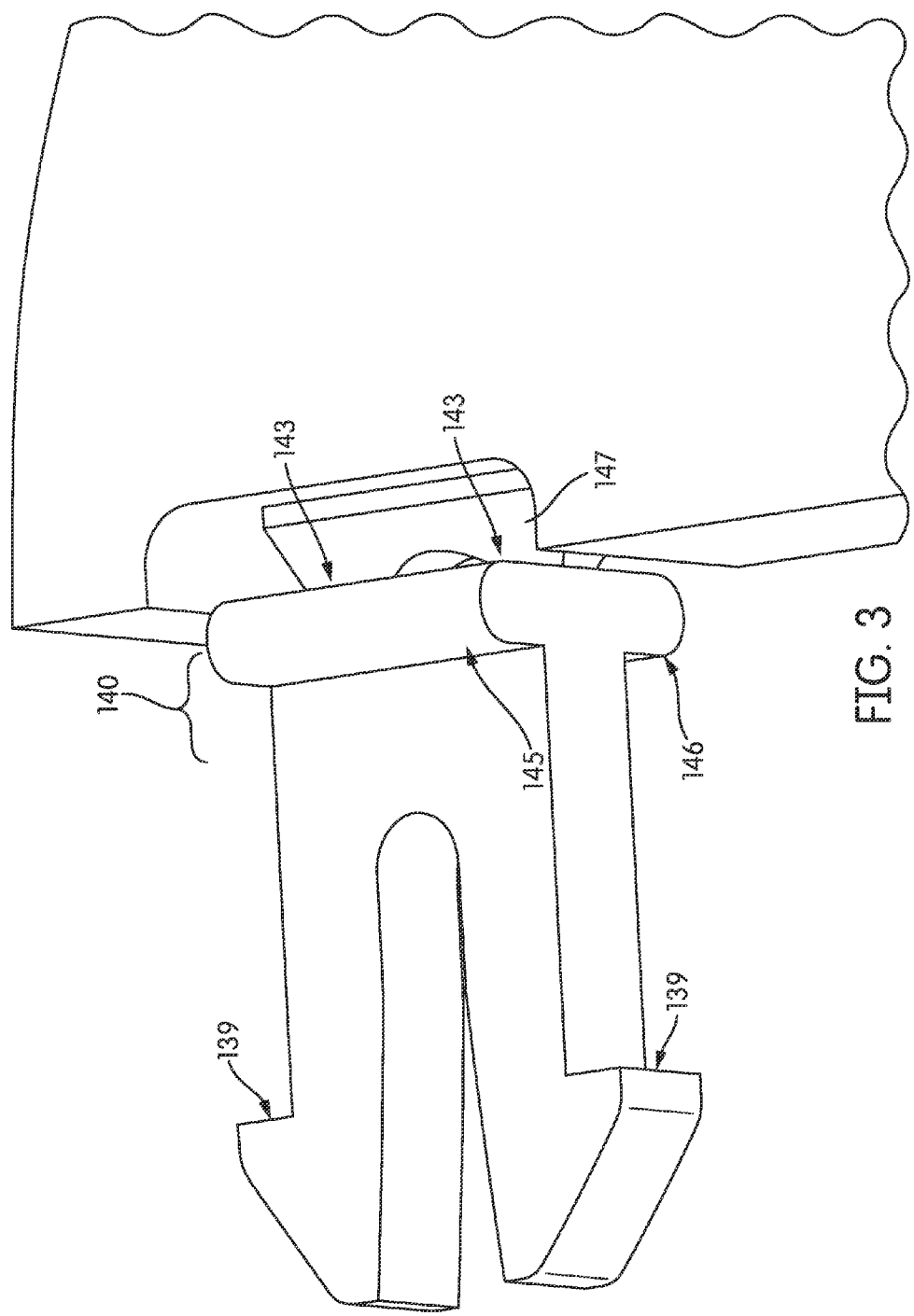
FIG. 3 is an enlarged view of frangible connection mechanism 140.

FIG. 3 is an enlarged view of frangible connection mechanism 140. As shown in FIG. 3, frangible connection mechanism includes a pair of vertically-extending lobes 145, 146, extending substantially orthogonal to the planar surface of lobe 122. Vertically-extending lobes 145, 146 are attached to ramped connector 147 to lobe 122. Ramped connector includes 2 narrow connection points 143, each connecting to vertically-extending lobes. This frangible connection mechanism 140 enables the frangible connection of projection 138 to lobe 122.

Fork-like projection 138 further includes an upper surface 142 and an opposing lower surface 144. Upper surface 142 faces the same direction as upper planar surface 126, but is not coplanar. Lower surface 144 aces the same direction with lower planar surface 130. Fork-like projection 138 further includes a plurality of extending tines 137, that extend initially laterally from an edge of forked projection 138 to produce an engaging shoulder 139, and then taper to provide an inclined engaging surface to enable locking of forked projection 138 with recess 148.

Lobe 124 has a corresponding recess 148 to receive fork-like projection 138. Each shoulder 139 on each extending tine 137 mates with a corresponding landing 149 formed in recess 148. In the manner shown in FIG. 4, lobes 122 and 124 are locked together by inserting fork-like projection 138 within recess 148 of lobe 124 through the use of corresponding shoulders 139 mating with corresponding landings 149 to prevent fork-like projection 138 from backing out of recess 148. Therefore, by locking lobes 122 and 124 together the first and second components 102 and 104 are locked together as well, and cannot be pulled apart along the longitudinal axis of fork-like projection 138.

As stated above, the locking mechanism used between the lobes 122 and 124 is a tamper evident locking mechanism. In other words, once components 102 and 104 are locked together, then the unlocking of the components is detectable. That is the tamper evident locking mechanism is a one time use locking mechanism that is destroyed upon components 102 and 104 being unlocked from one another. In that regard, components 102 and 104 are designed to provide a clean break from one another through the frangible connection mechanism 140. Components 102 and 104 are unlocked from one another by twisting, rotating, pulling, or otherwise creating stress between the components at the frangible connection created by narrow connection points 143. For example, a force may be applied to lobe 124 in the direction of arrow A1 and an opposing force applied to lobe 122 in the direction of arrow A2 to shear the narrow projection points 143 from vertically extending lobes 145, 146.

It should be noted that tag 100 is designed such that the frangible connection created by frangible connection mechanism 140 has a lower resistance to stress fracturing than any other portion of tag 100. As part of this design, FIGS. 1 and 4 show a slot 150 adjacent hinge 106 that remains between the first and second components 102, 104 when these components are locked together. Slot 150 acts as a stress relief structure such that when a user applies a force to break the tamper evident closure mechanism, the mechanism makes a clean break along narrow projection points 143 before any other portion of tag 100, including hinge 106, breaks. It is contemplated that any tag disclosed herein can have a surface texture that helps with gripping and/or leveraging of the tag in order to unlock the first and second components.

After unlocking components 102 and 104 from one another, the tamper evident locking mechanism cannot be used again. Consequently, the unlocking of components 102 and 104 from one another causes fork-like projection 138 to remain connected within recess 148 and shoulders 139 engaged with landings 149. In addition, narrow projection points 143 are so narrow that a clean break is made and there are no remnants of fork-like projection 138 on lobe 122. Therefore, evidence that components 102 and 104 cannot be locked together indicates tampering with tag 100 and/or the medical device captured by the tag. This provides a reliable and accurate mechanism for tracing and tracking the medical device encapsulated by tag 100.

Accordingly, tag 100 can be attached to and removed from a medical device with no component of tag 100 remaining permanently attached to the medical device. Furthermore, because fork-like projection 138 remains connected within recess 148 there are no loose portions or particulates of tag 100 that separate from the tag upon unlocking the tamper evident locking mechanism. Therefore, the tamper evident locking mechanism allows tag 100 to be attached to a medical device as a one-piece tag and be separated from the medical device as a one-piece tag.

The tags disclosed herein are only temporarily attached to the medical device and are utilized for tracking the use of and associated inventory levels of the medical devices. In that regard, prior to use of a medical device having such a tag, the tag is inspected for detectable evidence of the tamper evident locking mechanism being broken and/or the tag being removed from the medical device. If there are no signs of the tag being removed from the implant and/or the tamper evident locking mechanism being broken, then a healthcare provider can remove the tag from the implant by breaking the tamper evident locking mechanism thereby releasing the medical device from the tag. If there are signs that the tamper evident locking mechanism has been tampered with and/or other evidence that the tag may have been removed from the medical device, then the healthcare provider may elect not to use the medical device. Known implant holding devices that enable the release and re-capture of medical implants or devices cannot provide the healthcare provider with this type of information because there would be no way of knowing whether the medical implant or device was removed from its holder.

As discussed above, prior to use of the medical device, the tags are capable of having indicia readable by a computer. The computer readable indicia, such as a two dimensional barcode (or RFID tag) can be scanned to create a label containing the identifying information relating to the medical device captured by the tag. In the event that a tag cannot be scanned, the human readable indicia on the tag is utilized to create the label. Subsequently, the label is attached to a patient's medical chart. Thereafter, the tag is discarded after the corresponding label has printed. In this manner the tags disclosed herein are utilized to track implant use and associated inventory levels.

Figure 5:
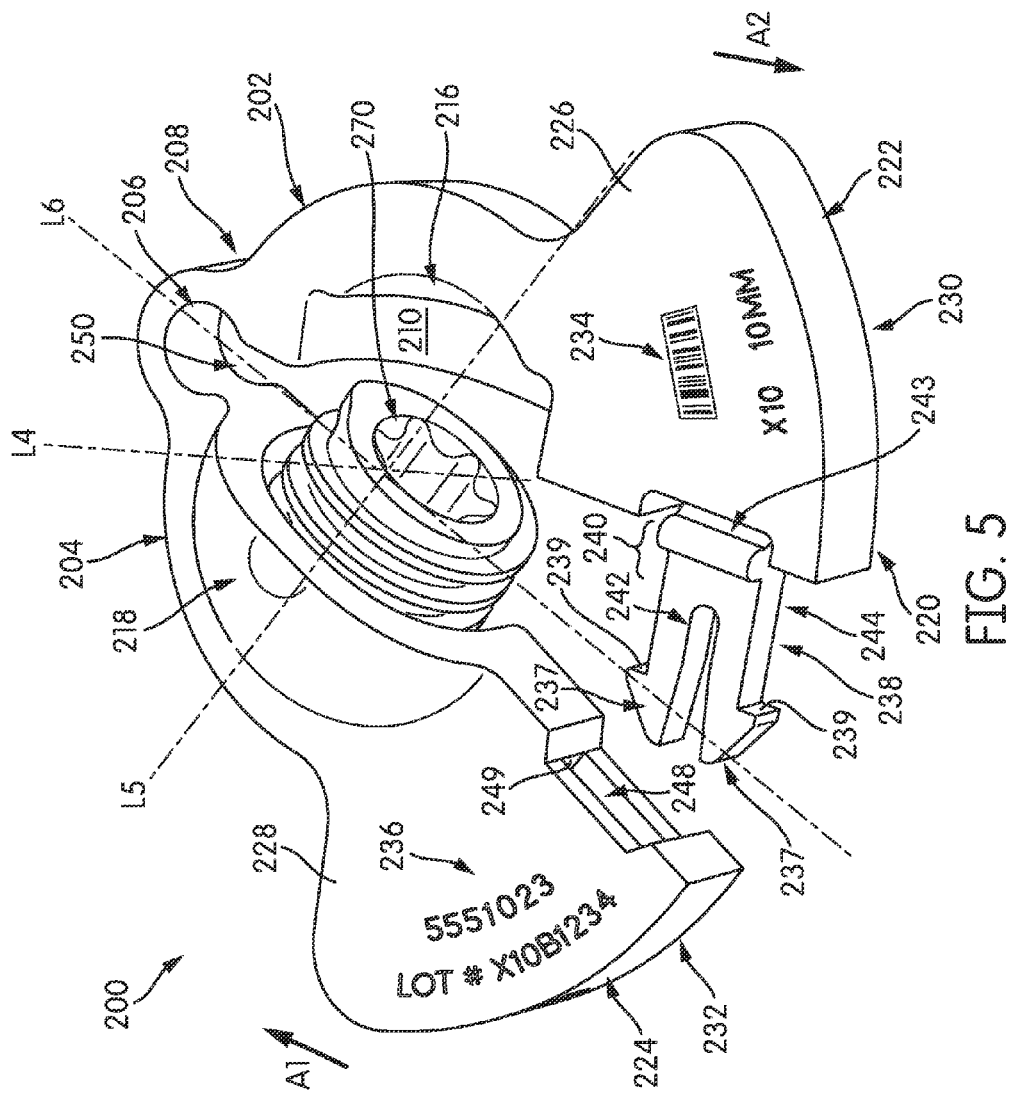
FIG. 5 is perspective view of a tag for attachment to a medical device according to another exemplary embodiment of the present disclosure.
Figure 6:
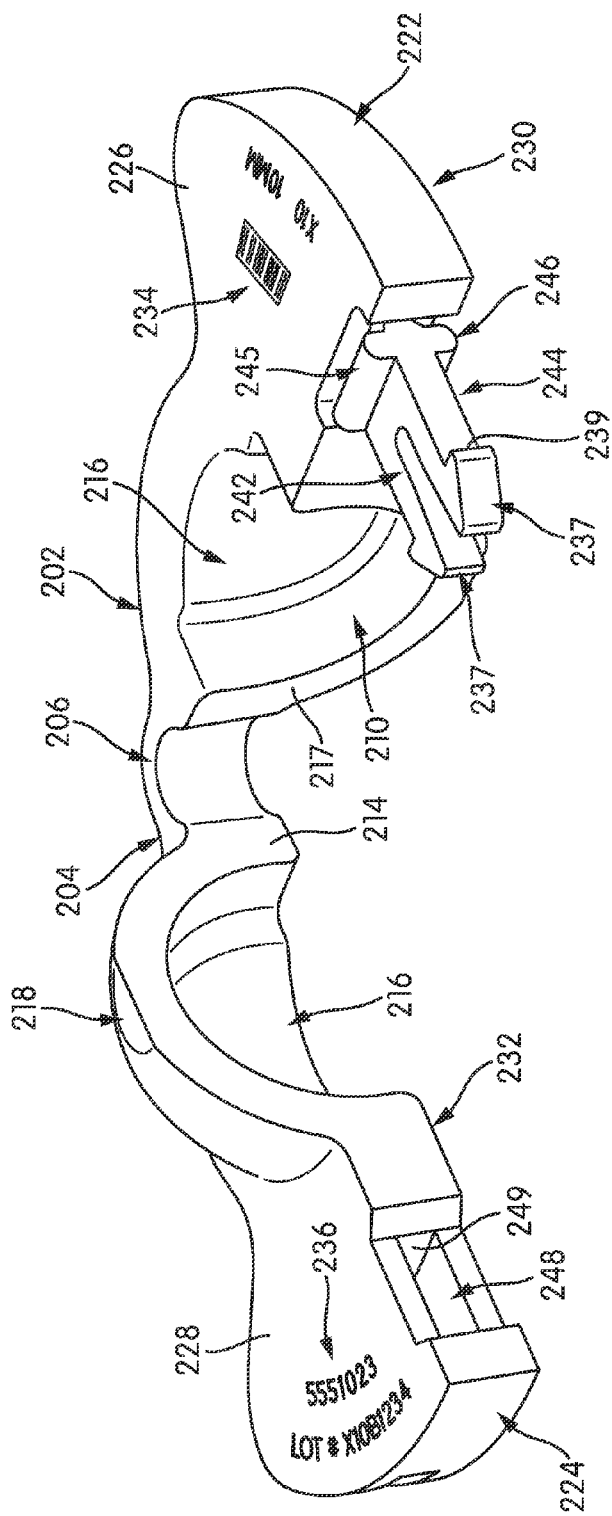
FIG. 6 is a perspective view of the tag of FIG. 5 where the tag is in an unlocked position.

Referring now to FIGS. 5 and 6, there is provided a perspective view of a tag 200 for attachment to a medical device is shown. Tag 200 is shown in an open or unlocked position ready to capture a medical device 270. Tag 200 has a first component 202 and a second component 204. A hinge or web 206 flexibly connects the first component 202 and the second component 204 to each other at a distal portion 208 of tag 200. Web 206 provides sufficient flexibility to allow first and second components to move relative to each other along axes L4 (y-axis), L5 (x-axis), L6 (z-axis) and any intervening axis. In that regard, web 206 allows the first component 202 and the second component 204 to remain attached to one another while the first and second components are positioned to capture a medical device therebetween.

Additionally, the distal portion of tag 200 defines an implant or medical device receiving cavity 210. In particular, portions 212 and 214 of first and second components 202, 204, respectively, define the implant receiving cavity 210. Cavity 210 has a cylindrical shape to receive a medical device with the corresponding shape. However, it is contemplated that cavity 210 can be any shape in order to accommodate the medical device. For example, implant receiving cavity 210 can be circular, square, rectangular, trapezoidal, oblong, cylindrical, triangular, and any other shape necessary to receive the medical device within the cavity 210.

Furthermore, device receiving cavity 21) is at least partially enclosed by projection 218, shown in FIG. 5 as having a partial dome-like configuration. Projection 218 serves to secure the medical device in place and prevent it from fatting out of tag 200 during transportation and handling. By virtue of partially enclosing medical device 270 with projection 218, when in the locked position, at least a portion of the medical device 270 will be somewhat exposed thereby enabling sterilization of the medical device. As a consequence, tag 200 or any other tag disclosed herein can be attached to a medical device undergoing sterilization. Moreover, device receiving cavity 210 preferably is larger than medical device 270 and may include, for example, laterally extending portions 216 (shown as a dome-shaped cavity in FIGS. 5 and 6) that extend beyond the medical device 270. Laterally extending portions 216 also enable any fluid (e.g. gas or liquid) used during a sterilization process to contact the medical device, and to drain from tag 200. In this manner, condensation and or other particulates present during sterilization are removed from tag 200. In an alternative embodiment, projection 218 my fully encapsulate the medical device 270, and projection 218 may be provided with one or more apertures to enable fluid (e.g., gas or liquid) used during a sterilization process to contact the medical device and drain from tag 200.

Tag 200 further comprises a pair of lobes 222 and 224 that extend from implant receiving cavity 210 toward a proximal portion 220 of tag 200. As shown in FIG. 5, lobes 222 and 224 extend substantially transverse from axis L4. However, lobes 222 and 224 can extend at any angle with respect to axis L4.

Lobes 222 and 224 have upper planar surfaces 226 and 228 and opposing tower surfaces 230 and 232, respectively. Upper planar surfaces 226 and 228 provide a relatively large planar surface with respect to any portion of a medical device capture by tag 200. In that manner, upper planar surfaces 226 and 228 provide an ideal surface for applying indicia or markings relevant to a medical device captured by tag 200.

As shown in FIG. 5, upper planar surface 226 and 228 contain indicia 234 and 236. Indicia 234 and 236 represent tracking devices capable of retaining identifying information, for example, relevant to the medical device captured by tag 200. Additionally, indicia 234 and 236 may represent identifying information related to the patient receiving the device, medical procedure used with the device, manufacturing information such as materials, processes, customer/supplier, and lot information of similarly manufactured devices. The identifying information is not intended to be limiting in scope by this disclosure, but instead is presented for exemplarily purposes only. Furthermore, any required manufacturing standards implanted requiring the marking of products with certain identifying information is considered to be within the scope of identifying information capable of be represented by indicia 234 and 236. Therefore, there is no need for the medical device captured by tag 200 to have identifying information because tag 200 provides any necessary identifying information.

In the present embodiment, indicia 234 and 236 represent a two dimensional bar code and alphanumeric lettering, respectively used to identify a medical device capture by tag 200. However, indicia 234 and 236, or any tracking device herein, may be any device that is capable of retaining identifying information. For example, the indicia can be a one or two dimensional barcode capable of being scanned by an optical scanner. Such an optical scanner may include a barcode scanner made by Baracoda such as the Evolution scanner (part number: B40160202).

Additionally, the tracking device or indicia may be in the form of a radio frequency identification (RFID) device built into the lobes of tag 200. Such a RFID device can transmit a radio frequency signal to an RFID transceiver that can obtain the identifying information of the medical device stored in the RFID device. Additionally, the indicia includes, for example, human readable information and/or data that may include visual alphanumeric characters and tactile features such as different surface textures and/or raised or lowered portions. Furthermore, the lobes 222 and 224 can include a sealable groove, slot, or compartment that has a transparent cover such that any human and/or computer readable information can be placed into the sealable groove, slot, or compartment, but can still be read through upper planar surfaces 226 and 228. In addition, the indicia may include a printed adhesive label in either human and/or computer readable form that is resistant to sterilization procedures.

Although indicia 234 and 236 are shown as two separate types of tracking devices, the identifying information contained within these indicia may contain the same amount of identifying information. However, it is also possible that one indicia may provide more identifying information than the other indicia. Additionally, there may be only one indicia on either lobe 222 or lobe 224, but not the other lobe. Likewise, the same type of indicia may be represented on both lobes 222 and 224. Even more, lobes 222 and 224 may have only one indicia that spans consecutively across both upper planar surfaces 226 and 228.

Lobes 222 and 224 further contain a tamper evident locking mechanism that locks the first component 202 to the second component 204. Preferably, lobe 222 has a fork-like projection 238 located on the most proximal portion of tag 200. Fork-like projection 238 has a frangible connection to lobe 222. The frangible connection is created by a connection mechanism 240 extending along the width W of fork-like projection 238 at its connection with lobe 222. The connection mechanism 240 shown in FIG. 5 has the same features as the connection mechanism 140 shown in the enlarged view of FIG. 3. The description of connection mechanism 140 as it pertains to the embodiment of FIGS. 1 and 2, applies equally to the connection mechanism 240, as it applies to FIGS. 5 and 6.

Fork-like projection 238 further includes an upper surface 242 and an opposing lower surface 244. Upper surface 242 faces the same direction as upper planar surface 226, but is not coplanar. Lower surface 244 aces the same direction with lower planar surface 230. Fork-like projection 238 further includes a plurality of extending tines 237, that extend initially laterally from an edge of forked projection 238 to produce an engaging shoulder 239, and then taper to provide an inclined engaging surface to enable locking of forked projection 238 with recess 248.

Lobe 224 has a corresponding recess 248 to receive fork-like projection 238. Each shoulder 239 on each extending tine 237 mates with a corresponding landing 249 formed in recess 248. Lobes 222 and 224 thus can be locked together by inserting fork-like projection 238 within recess 248 of lobe 224 through the use of corresponding shoulders 239 mating with corresponding landings 249 to prevent fork-like projection 238 from backing out of recess 248. Therefore, by locking lobes 222 and 224 together the first and second components 202 and 204 are locked together as well, and cannot be pulled apart along the longitudinal axis of fork-like projection 238.

As stated above, the locking mechanism used between the lobes 222 and 224 is a tamper evident locking mechanism. In other words, once components 202 and 204 are locked together, then the unlocking of the components is detectable. That is the tamper evident locking mechanism is a one time use locking mechanism that is destroyed upon components 202 and 204 being unlocked from one another. In that regard, components 202 and 204 are designed to provide a clean break from one another through the frangible connection mechanism 240. Components 202 and 204 are unlocked from one another by twisting, rotating, pulling, or otherwise creating stress between the components at the frangible connection created by narrow connection points 243. For example, a force may be applied to lobe 224 in the direction of arrow A1 and an opposing force applied to lobe 222 in the direction of arrow A2 to shear the narrow projection points 243 from vertically extending lobes 245, 246.

It should be noted that tag 200 is designed such that the frangible connection created by frangible connection mechanism 240 has a lower resistance to stress fracturing than any other portion of tag 200. As part of this design, FIG. 5 shows a slot 250 adjacent hinge 206 that remains between the first and second components 202, 204 when these components are locked together. Slot 250 acts as a stress relief structure such that when a user applies a force to break the tamper evident closure mechanism, the mechanism makes a clean break along narrow projection points 243 before any other portion of tag 200, including hinge 206, breaks. It is contemplated that any tag disclosed herein can have a surface texture that helps with gripping and/or leveraging of the tag in order to unlock the first and second components.

After unlocking components 202 and 204 from one another, the tamper evident locking mechanism cannot be used again. In that regard, the unlocking of components 202 and 204 from one another causes fork-like projection 238 to remain connected within recess 248 and shoulders 239 engaged with landings 249. In addition, narrow projection points 243 are so narrow that a clean break is made and there are no remnants of fork-like projection 238 on lobe 222. Therefore, evidence that components 202 and 204 cannot be locked together indicates tampering with tag 200 and/or the medical device captured by the tag. This provides a reliable and accurate mechanism for tracing and tracking the medical device encapsulated by tag 200.

Accordingly, tag 200 can be attached and removed from a medical device with no component of tag 200 remaining permanently attached to the medical device. Furthermore, because fork-like projection 238 remains connected within recess 248 there are no loose portions or particulates of tag 200 that separate from the tag upon unlocking the tamper evident locking mechanism. Therefore, the tamper evident locking mechanism allows tag 200 to be attached to a medical device as a one-piece tag and be separated from the medical device as a one-piece tag.

Figure 7:
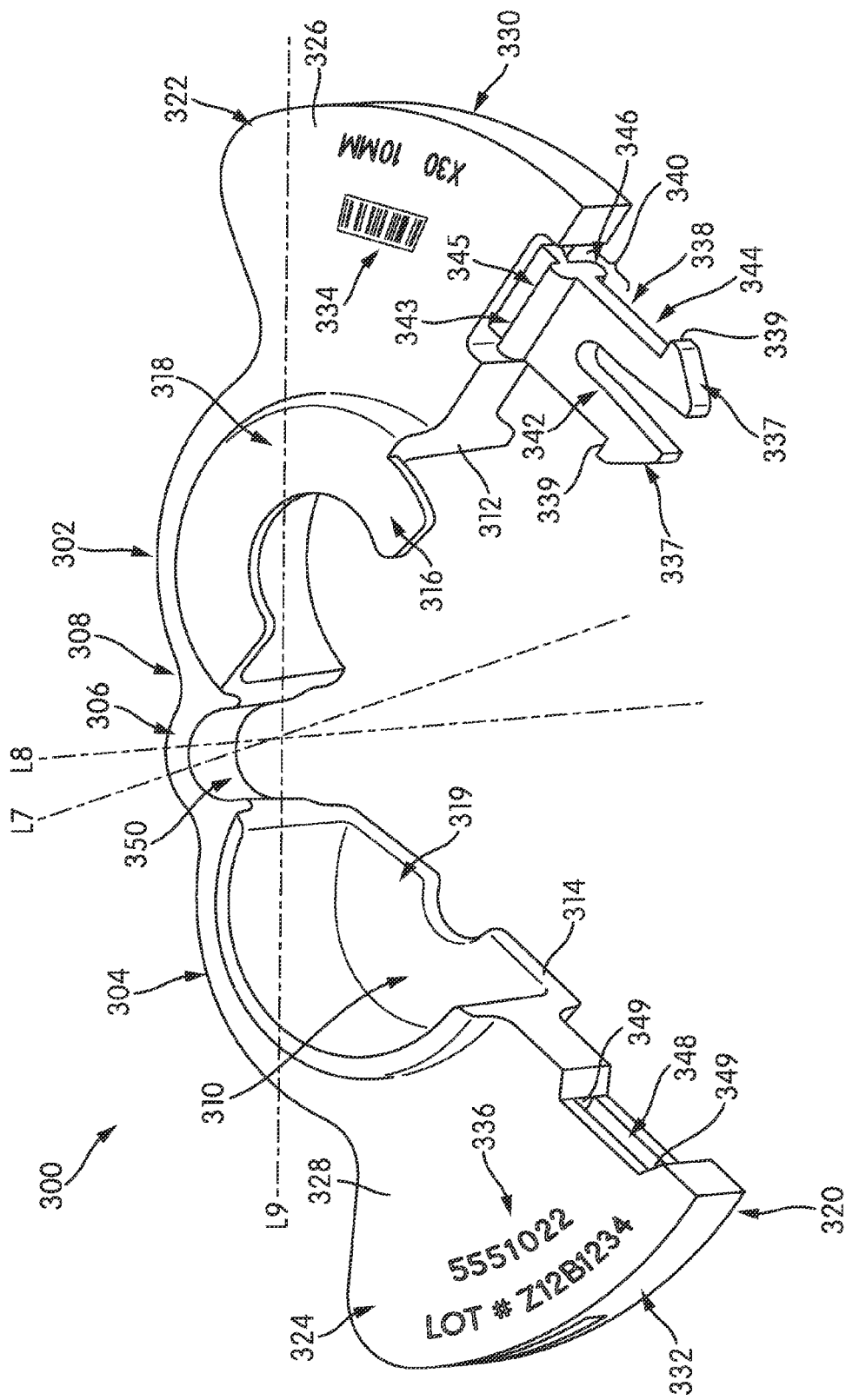
FIG. 7 is a perspective view of a tag for attachment to a medical device according to another exemplary embodiment of the present disclosure.
Figure 8:
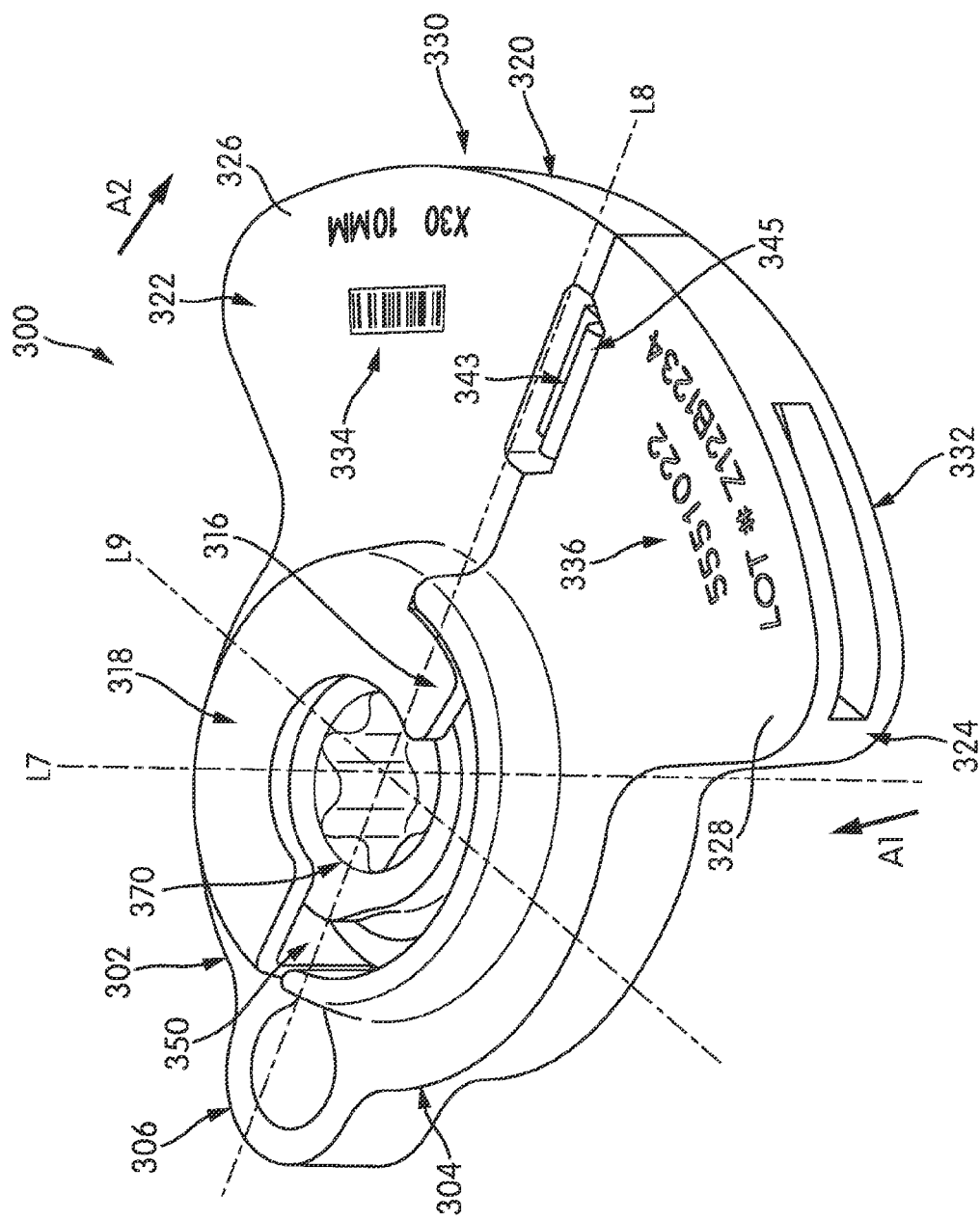
FIG. 8 is a side view of the tag of FIG. 7 where the tag is in a locked position.

Referring now to FIGS. 7 and 8, there is provided a perspective view of a tag 300 for attachment to a medical device is shown. Tag 300 is shown in an open or unlocked position ready to capture a medical device 370. Tag 300 has a first component 302 and a second component 304. A hinge or web 306 flexibly connects the first component 302 and the second component 304 to each other at a distal portion 308 of tag 300. Web 306 provides sufficient flexibility to allow first and second components to move relative to each other along axes L7 (y-axis), L8 (x-axis), L9 (z-axis) and any intervening axis. In that regard, web 306 allows the first component 302 and the second component 304 to remain attached to one another while the first and second components are positioned to capture a medical device therebetween.

Additionally, the distal portion of tag 300 defines an implant or medical device receiving cavity 310. In particular, portions 312 and 314 of first and second components 302, 304, respectively, define the implant receiving cavity 310. Cavity 310 has a cylindrical shape to receive a medical device with the corresponding shape. However, it is contemplated that cavity 310 can be any shape in order to accommodate the medical device. For example, device receiving cavity 310 can be circular, square, rectangular, trapezoidal, oblong, cylindrical, triangular, and any other shape necessary to receive the medical device within the cavity 310.

Furthermore, device receiving cavity 310 is at least partially enclosed by projection 318, shown in FIG. 7 as having a thin protrusion 316. Projection 318 and thin protrusion 316 serve to secure the medical device in place and prevent it from falling out of tag 300 during transportation and handling. By virtue of partially enclosing medical device 370 with projection 318 and thin protrusion 316, when in the locked position (FIG. 8), at least a portion of the medical device 370 will be somewhat exposed thereby enabling sterilization of the medical device. As a consequence, tag 300 or any other tag disclosed herein can be attached to a medical device undergoing sterilization. Moreover, device receiving cavity 310 preferably is slightly larger than medical device 270 to enable any fluid (e.g. gas or liquid) used during a sterilization process to contact the medical device, and to drain from tag 300. In this manner, condensation and or other particulates present during sterilization are removed from tag 300. In an alternative embodiment, projection 318 and bottom 319 may fully encapsulate the medical device 370, and projection 318 and/or bottom 319 may be provided with one or more apertures to enable fluid (e.g., gas or liquid) used during a sterilization process to contact the medical device and drain from tag 300.

Tag 300 further comprises a pair of lobes 322 and 324 that extend from implant receiving cavity 310 toward a proximal portion 320 of tag 300. As shown in FIG. 7, lobes 322 and 324 extend substantially transverse from axis L7. However, lobes 322 and 324 can extend at any angle with respect to axis L4.

Lobes 322 and 324 have upper planar surfaces 326 and 328 and opposing lower surfaces 330 and 332, respectively. Upper planar surfaces 326 and 328 provide a relatively large planar surface with respect to any portion of a medical device capture by tag 300. In that manner, upper planar surfaces 326 and 328 provide an ideal surface for applying indicia or markings relevant to a medical device captured by tag 200.

As shown in FIG. 7, upper planar surface 326 and 328 contain indicia 334 and 336. Indicia 334 and 336 represent tracking devices capable of retaining identifying information, for example, relevant to the medical device captured by tag 300. Additionally, indicia 334 and 336 may represent identifying information related to the patient receiving the device, medical procedure used with the device, manufacturing information such as materials, processes, customer/supplier, and lot information of similarly manufactured devices. The identifying information is not intended to be limiting in scope by this disclosure, but instead is presented for exemplarily purposes only. Furthermore, any required manufacturing standards implanted requiring the marking of products with certain identifying information is considered to be within the scope of identifying information capable of be represented by indicia 334 and 336. Therefore, there is no need for the medical device captured by tag 300 to have identifying information because tag 300 provides any necessary identifying information.

In the present embodiment, indicia 334 and 336 represent a two dimensional bar code and alphanumeric lettering, respectively used to identify a medical device capture by tag 300. However, indicia 334 and 336, or any tracking device herein, may be any device that is capable of retaining identifying information. For example, the indicia can be a one or two dimensional barcode capable of being scanned by an optical scanner. Such an optical scanner may include a barcode scanner made by Baracoda such as the Evolution scanner (part number: B40160202).

Additionally, the tracking device or indicia may be in the form of a radio frequency identification (RFID) device built into the lobes of tag 300. Such a RFID device can transmit a radio frequency signal to an RFID transceiver that can obtain the identifying information of the medical device stored in the RFID device. Additionally, the indicia includes, for example, human readable information and/or data that may include visual alphanumeric characters and tactile features such as different surface textures and/or raised or lowered portions. Furthermore, the lobes 322 and 324 can include a sealable groove, slot, or compartment that has a transparent cover such that any human and/or computer readable information can be placed into the sealable groove, slot, or compartment, but can still be read through upper planar surfaces 326 and 328. In addition, the indicia may include a printed adhesive label in either human and/or computer readable form that is resistant to sterilization procedures.

Although indicia 334 and 336 are shown as two separate types of tracking devices, the identifying information contained within these indicia may contain the same amount of identifying information. However, it is also possible that one indicia may provide more identifying information than the other indicia. Additionally, there may be only one indicia on either lobe 322 or lobe 324, but not the other lobe. Likewise, the same type of indicia may be represented on both lobes 322 and 324. Even more, lobes 322 and 324 may have only one indicia that spans consecutively across both upper planar surfaces 326 and 328.

Lobes 322 and 324 further contain a tamper evident locking mechanism that locks the first component 302 to the second component 304. Preferably, lobe 322 has a fork-like projection 338 located on the most proximal portion of tag 300. Fork-like projection 338 has a frangible connection to lobe 322. The frangible connection is created by a connection mechanism 340 extending along the width W of fork-like projection 338 at its connection with lobe 322. The connection mechanism 340 shown in FIG. 7 has the same features as the connection mechanism 140 shown in the enlarged view of FIG. 3. The description of connection mechanism 140 as it pertains to the embodiment of FIGS. 1 and 2, applies equally to the connection mechanism 340, as it applies to FIGS. 7 and 8.

Fork-like projection 338 further includes an upper surface 342 and an opposing lower surface 344. Upper surface 342 faces the same direction as upper planar surface 326, but is not coplanar. Lower surface 344 faces the same direction with lower planar surface 330. Fork-like projection 338 further includes a plurality of extending tines 337, that extend initially laterally from an edge of forked projection 338 to produce an engaging shoulder 339, and then taper to provide an inclined engaging surface to enable locking of forked projection 338 with recess 348.

Lobe 324 has a corresponding recess 348 to receive fork-like projection 338. Each shoulder 339 on each extending tine 337 mates with a corresponding landing 349 formed in recess 348. Lobes 322 and 324 thus can be locked together by inserting fork-like projection 338 within recess 348 of lobe 324 through the use of corresponding shoulders 339 mating with corresponding landings 349 to prevent fork-like projection 338 from backing out of recess 348. Therefore, by locking lobes 322 and 324 together the first and second components 302 and 304 are locked together as well, and cannot be pulled apart along the longitudinal axis of fork-like projection 338.

As stated above, the locking mechanism used between the lobes 322 and 324 is a tamper evident locking mechanism. In other words, once components 302 and 304 are locked together, then the unlocking of the components is detectable. That is the tamper evident locking mechanism is a one time use locking mechanism that is destroyed upon components 302 and 304 being unlocked from one another. In that regard, components 302 and 304 are designed to provide a clean break from one another through the frangible connection mechanism 340. Components 302 and 304 are unlocked from one another by twisting, rotating, pulling, or otherwise creating stress between the components at the frangible connection created by narrow connection points 343. For example, a force may be applied to lobe 324 in the direction of arrow A1 and an opposing force applied to lobe 322 in the direction of arrow A2 to shear the narrow projection points 343 from vertically extending lobes 345, 346.

It should be noted that tag 300 is designed such that the frangible connection created by frangible connection mechanism 340 has a lower resistance to stress fracturing than any other portion of tag 300. As part of this design, FIGS. 7 and 8 show a slot 350 adjacent hinge 306 that remains between the first and second components 302, 304 when these components are locked together. Slot 350 acts as a stress relief structure such that when a user applies a force to break the tamper evident closure mechanism, the mechanism makes a clean break along narrow projection points 343 before any other portion of tag 300, including hinge 306, breaks. It is contemplated that any tag disclosed herein can have a surface texture that helps with gripping and/or leveraging of the tag in order to unlock the first and second components.

After unlocking components 302 and 304 from one another, the tamper evident locking mechanism cannot be used again. In that regard, the unlocking of components 302 and 304 from one another causes fork-like projection 338 to remain connected within recess 348 and shoulders 339 engaged with landings 349. In addition, narrow projection points 343 are so narrow that a clean break is made and there are no remnants of fork-like projection 338 on lobe 322. Therefore, evidence that components 302 and 304 cannot be locked together indicates tampering with tag 300 and/or the medical device captured by the tag. This provides a reliable and accurate mechanism for tracing and tracking the medical device encapsulated by tag 300.

Accordingly, tag 300 can be attached and removed from a medical device with no component of tag 300 remaining permanently attached to the medical device. Furthermore, because fork-like projection 338 remains connected within recess 348 there are no loose portions or particulates of tag 300 that separate from the tag upon unlocking the tamper evident locking mechanism. Therefore, the tamper evident locking mechanism allows tag 300 to be attached to a medical device as a one-piece tag and be separated from the medical device as a one-piece tag.

It should be noted the tamper evident locking mechanism for locking the various first and second components discussed above may be accomplished, without limitation, by applying adhesive between the components. Additionally, the tamper evident locking mechanism for locking the various first and second components discussed above may be accomplished, without limitation, by melting, welding, ultrasonic welding or otherwise joining all or a portion of the components together.

Furthermore, the tamper evident locking mechanism for locking the various first and second components discussed above may include an indicator device across a joint between or through the components that fracture, change shape, change color, or otherwise are altered by separation of the first and second components. Detectable separation of the components may occur at one or more connections between the components, or may include fracture or change within either or both of the first and second components.

The tags disclosed herein are in whole or in part may be constructed of biocompatible materials of various types including metals or polymers. For example, the tags may be made in whole or in part of a polymer known as Radel R. In such a scenario, a tag is formed in whole or in part using Radel R polymer mixed with barium sulfate ($BaSO_4$). In this manner, the tag is radiopaque such that incase of accidental implantation the tag can be located via an x-ray, for example. Further, examples of tag materials include, but are not limited to, non-cobalt-chromium alloys, titanium alloys, nickel titanium alloys, and/or stainless steel alloys, plastics and polymers including without limitation any member of the polyaryletherketone (PAEK) family such as polyetheretherketone (PEEK), carbon-reinforced PEEK, or polyetherketoneketone (PEKK); polysulforte; polyetherimide; polyimide; ultra-high molecular weight polyethylene (UHMWPE); and/or cross-linked UHMWPE.

Although the tags described herein are used to track and trace a bone screw (FIGS. 1, 2, 4, 5, and 8), this is no way implies a limitation of such medical devices the tags can be associated with and used to track. The medical device capable of being tracked by the tags described herein may be any implant or instrument used in a medical procedure. In that regard, the medical device of some embodiments may be, without limitation, a surgical screw of any variety, a spinal or other orthopedic plate, a surgical rod, an interbody spinal device, a vertebral disc arthroplasty device, a nucleus replacement device, a corpectomy device, a vertebrectomy device, a mesh device, a facet fixation or arthroplasty device, a structural bone graft, a staple, a tether of synthetic material or wire, or other spinal fixation instrumentation, an intramedullary nail, an external fixation device, a hip prosthesis or therapeutic device, a knee prosthesis or therapeutic device, or an instrument useful with any of the previously recited devices.

The tags and indicia and medical devices described herein are capable of undergoing one or more steam sterilization cycles, or other sterilization procedures such as radiation or gas sterilization, without degrading in a manner that would make the tag unusable and the implant unsuitable for use in a medical procedure. Therefore, the medical devices can be shipped non-sterilized from the manufacture to a healthcare provider, but the non-sterile medical device can still be tracked for inventory purposes and uses thereof through the use of the tags described herein.

The medical device of this or any other embodiment of the invention may consist of materials, by way of example, and without limitation, including titanium and its alloys, ASTM material, cobalt chrome, tantalum, ceramic, poly-ether-ether-ketone (PEEK), PEAK, various plastics, plastic composites, carbon fiber composites, coral, allograft, autograft, zenograft, and can include artificial materials which are at least in part bioresorbable, or any material suitable for human implantation.

While the present invention has been illustrated by the above description of embodiments, and while the embodiments have been described in some detail, it is not the intention of the applicant to restrict or in any way limit the scope of the invention to such detail. Additional advantages and modifications will readily appear to those skilled in the art. Therefore, the invention in its broader aspects is not limited to the specific details, representative apparatus and methods, and illustrative examples shown and described. Accordingly, departures may be made from such details without departing from the spirit or scope of the applicant's general or inventive concept. It is understood that all spatial references, such as "longitudinal axis," "horizontal," "vertical," "top," "upper," "lower," "bottom," "left," and "right," are for illustrative purposes only and can be varied within the scope of the disclosure.

What is claimed is:

1. A tag for tracking inventory levels and uses of an implant, the tag comprising:
    a first component having a proximal portion and a distal portion;
    a second component having a proximal portion and distal portion,
    an implant receiving cavity formed by the distal portion of the first component and the distal portion of the second component wherein the implant receiving cavity includes an encapsulating extension to substantially encapsulate an implant;
    a planar surface formed by the proximal portion of the first component and the proximal portion of the second component, the planar surface extending from the implant receiving cavity such that the planar surface is substantially transverse to a longitudinal axis of the implant received within the implant receiving cavity, the planar surface including indicia; and
    a tamper evident locking mechanism configured for locking the first component to the second component,
    wherein at least a portion of the first and second components is radiopaque,
    wherein the distal portion of the first component further includes at least one frangible connection mechanism, the at least one frangible connection mechanism ensures that the first and second components separate along a fracture plane that is substantially transverse to a midline of the implant receiving cavity and includes a portion of the tamper evident locking mechanism,
    wherein the frangible connection mechanism comprises a pair of vertically extending lobes extending substantially orthogonal to the planar surface formed by the proximal portion of the first component and the proximal portion of the second component, a ramped connector attached to the pair of vertically extending lobes wherein the ramped connection is attached at least one narrow connection point.

2. The tag of claim 1, wherein the encapsulating extension comprises one or more extending slots.

3. The tag of claim 1, wherein the encapsulating extension comprises one or more apertures.

4. The tag of claim 1, wherein the tag comprises a material capable of undergoing sterilization without degradation such that the indicia remains readable after sterilization of the tag, the indicia includes at least one of a human readable and computer readable form.

5. The tag of claim 1, wherein the indicia provides identifying information relating to at least one of the implant, a patient receiving the implant, a medical procedure used with the implant, and a material and process of manufacturing associated with the implant.

6. The tag of claim 1, wherein the tamper evident locking mechanism provides an unlocked position for receiving an implant between the first and second components within the implant receiving cavity and a locked position in which the first and second components are locked together preventing the implant from being released from the cavity without detectable evidence.

7. The tag of claim 1, wherein at least a portion of the first and second components forming the implant receiving cavity includes a plurality of apertures allowing particulate to drain away from the cavity and the implant received within the cavity while the implant with the tag coupled thereto undergo sterilization.

8. The tag of claim 1, wherein the tamper evident locking mechanism is comprised of a fork-like projection comprising a plurality of tines positioned on the distal portion of the first component, and a corresponding recess positioned on the distal portion of the second component.

9. The tag of claim 8, wherein each tine on the fork-like projection comprises a shoulder, wherein the corresponding recess comprises at least one landing for each shoulder, and wherein when in the locked position, each shoulder engages a corresponding landing to prevent the forklike projection from backing out of the recess.

10. The tag of claim 1, wherein the frangible connection mechanism is positioned between a fork-like projection and the first component, and when the frangible connection mechanism is broken, the frangible connection mechanism breaks at the at least one narrow connection point.

11. The tag of claim 1, wherein the indicia is positioned on the lobes.

12. The tag of claim 1, wherein the indicia is selected from the group consisting of a one dimensional barcode, a two dimensional barcode, or a radio frequency identification device.

13. A system comprising:
a tag for tracking inventory levels and uses of an implant comprising:
a first component having a proximal portion and a distal portion;
a second component having a proximal portion and distal portion,
an implant receiving cavity formed by the distal portion of the first component and the distal portion of the second component, wherein the implant receiving cavity includes an encapsulating extension to substantially encapsulate an implant;
a planar surface formed by the proximal portion of the first component and the proximal portion of the second component, the planar surface extending from the implant receiving cavity such that the planar surface is substantially transverse to a longitudinal axis of the implant received within the implant receiving cavity, the planar surface including indicia; and
a tamper evident locking mechanism configured for locking the first component to the second component,
wherein at least a portion of the first and second components is radiopaque; and
an implant positioned within the implant receiving cavity of the tag,
wherein the distal portion of the first component further includes at least one frangible connection mechanism, the at least one frangible connection mechanism ensures that the first and second components separate along a fracture plane that is substantially transverse to a midline of the implant receiving cavity and includes a portion of the tamper evident locking mechanism,
wherein the frangible connection mechanism comprises a pair of vertically extending lobes extending substantially orthogonal to the planar surface formed by the proximal portion of the first component and the proximal portion of the second component a ramped connector attached to the pair of vertically extending lobes wherein the ramped connection is attached at least one narrow connection point.

14. The system as claimed in claim 13, wherein the implant is selected from the group consisting of a surgical screw, a spinal plate, an orthopedic plate, a surgical rod, an interbody spinal device, a vertebral disc arthroplasty device, a nucleus replacement device, a corpectomy device, a vertebrectomy device, a mesh device, a facet fixation or arthroplasty device, a structural bone graft, a staple, a tether of synthetic material or wire, an intramedullary nail, an external fixation device, a hip prosthesis, a knee prosthesis, and combinations thereof.

15. The system as claimed in claim 13, wherein the tamper evident locking mechanism provides an unlocked position for receiving an implant between the first and second components within the implant receiving cavity and a locked position in which the first and second components are locked together preventing the implant from being released from the cavity without detectable evidence.

16. The system of claim 13, wherein the tamper evident locking mechanism is comprised of a fork-like projection comprising a plurality of tines positioned on the distal portion of the first component, and a corresponding recess positioned on the distal portion of the second component.

17. The system of claim 16, wherein each tine on the fork-like projection comprises a shoulder, wherein the corresponding recess comprises at least one landing for each shoulder, and wherein when in the locked position, each shoulder engages a corresponding landing to prevent the fork-like projection from backing out of the recess.

18. The system of claim 13, wherein the frangible connection mechanism is positioned between a fork-like projection and the first component, and when the frangible connection mechanism is broken, the frangible connection mechanism breaks at the at least one narrow connection point.

19. The system of claim 13, wherein the indicia is positioned on the lobes.

* * * * *